United States Patent [19]

Lee et al.

[11] Patent Number: 5,155,226
[45] Date of Patent: Oct. 13, 1992

[54] METHOD FOR THE PREPARATION OF 9-AMINO-1,2,3,4-TETRAHYDROACRIDINE

[75] Inventors: Thomas B. K. Lee, Whitehouse Station; Keith E. Goehring, Piscataway, both of N.J.

[73] Assignee: Hoechst-Roussel Pharmaceuticals Incorporated, Somerville, N.J.

[21] Appl. No.: 656,389

[22] Filed: Feb. 19, 1991

[51] Int. Cl.$^5$ .......................................... C07D 219/08
[52] U.S. Cl. .................................................... 546/105
[58] Field of Search ...................... 546/105; 514/297

[56] References Cited

PUBLICATIONS

Sujan Singh et al., A Sample and Versatile Heterocyclic Synthesis from Aminoitriles and Ketones, J. Het. Chem., vol. 5, 1968, pp. 737-739.

N. S. Girgis et al., Phosphorus Pentoxide in Organics Synthesis, Synthesis, 1985, pp. 547-548.

*Primary Examiner*—Nicholas S. Rizzo
*Attorney, Agent, or Firm*—Elliott Korsen

[57] ABSTRACT

A method of preparing 9-amino-1,2,3,4-tetrahydroacridine by the reaction of 2-aminobenzonitrile and cyclohexanone with p-toluenesulfonic acid monohydrate in xylenes is disclosed.

5 Claims, No Drawings

METHOD FOR THE PREPARATION OF 9-AMINO-1,2,3,4-TETRAHYDROACRIDINE

The present invention relates to a new method of preparing 9-amino-1,2,3,4-tetrahydroacridine of the formula

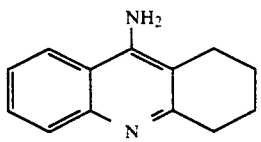

by the reaction of 2-aminobenzonitrile and cyclohexanone with p-toluenesulfonic acid monohydrate in xylenes. The free base can be easily converted to the hydrochloride salt, known as tacrine by reaction with hydrochloric acid.

Tacrine has been shown to be potentially useful in the treatment of various memory dysfunctions characterized by a decreased cholinergic function, such as Alzheimer's disease.

The invention involves the facile synthesis of tacrine by reacting 2-aminobenzonitrile of the formula:

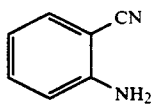

with cyclohexanone in the presence of over 1equiv of p-toluenesulfonic acid monohydrate in xylenes.

The preparation of tacrine and its derivatives is well known.

The Journal of Heterocyclic Chemistry, vol. 5, 1968, pp 737-39 discloses the synthesis of tetrahydroacridones using p-toluenesulfonic acid in the following reaction:

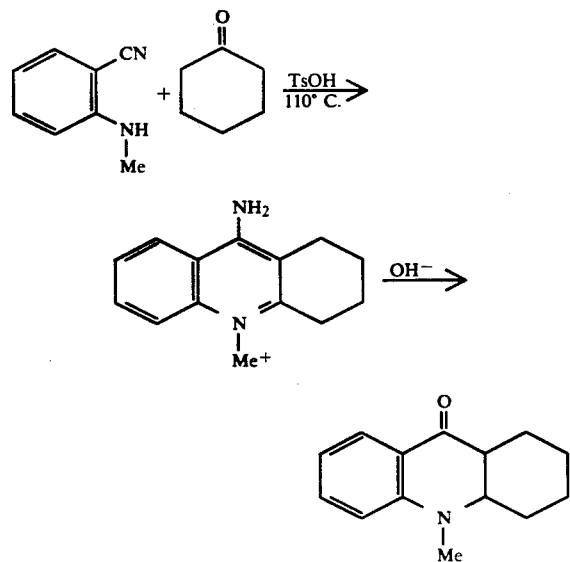

J. Bielavsky in Collection Czechoslov Chem. Commun., vol. 42, 1977, pp 2802-2808 discloses the preparation of analogues of tacrine by Hofmann degradation of amides. In particular, it is claimed as an advantageous method for the preparation of tacrine. However, it only produces a yield of about 65%.

Tetrahedron Letters, no. 20, 1963, pp. 1277-81, discloses a direct synthesis of aminoquinolines including tacrine. However, this method involves the use of zinc chloride and extremely high temperatures.

Tetrahedron Letters, no. 27 1986, pp. 5323-26 teaches the synthesis of the tetrahydroacridine from an imine using 2.0 equiv of lithium diisopropylamide (LDA) in tetrahydrofuran. This reference however, does not teach the synthesis of tacrine.

Synthesis, 1985, pp. 547-8 discloses the synthesis of tacrine in only 30% yield using phosphorus pentoxide.

None of the above cited methods of preparation have the advantages of the instant invention which provides high yield and high purity of the product.

Some of the advantages of this novel method include:

1) The convenience of a one step process which can be used for the commercial production of this important compound;

2) the ability to obtain tacrine in high yield;

3) the process is environmentally safe because it does not involve the use of toxic metals such as zinc;

4) the process is run at a temperature of less than 150° C. which can be conveniently carried out as a production batch process;

5) the solvent xylenes is easily recoverable and recyclable which contributes to the cost and environmental effectiveness of the process; and 6) the method is easily worked up with no volatile gaseous reagents or by-products produced as in, for instance, the method employing phosphorus oxychloride, or ammonia and bromine in the Hoffmann degradation of amides. All of these advantages make this an improved process over the prior art.

Tacrine is prepared according to the following reaction:

A solution of 2-aminobenzonitrile in xylenes with 0.02-0.05 equiv of p-toluenesulfonic acid monohydrate is heated to reflux with stirring. At reflux, cyclohexanone in xylenes is added. The mixture is refluxed for 8 to 12 hours, cooled and another 1.0-1.5 equiv of p-toluenesulfonic acid monohydrate is added. The mixture is heated to reflux for 3 to 7 hours. The product, as a p-toluenesulfonic acid salt, is isolated by filtration. Basification of this product with aqueous sodium hydroxide and extraction with dichloromethane provide the desired product, tacrine, as a free base.

This process can be carried out in a number of different types of solvents such as aromatic hydrocarbons, halogenated aromatics or aromatic ethers. Examples of aromatic hydrocarbons are xylenes, toluene and mesitylene. Examples of suitable halogenated solvents are chlorobenzene, p-, m- or o-dicholorobenzenes and 2-, 3- or 4-chlorotoluenes. Aromatic ethers which can be used in this process include anisole, p-, m-, or o-dimethoxybenzenes and 2-, 3- or 4-methylanisole. The preferred solvent is xylenes, as a mixture of p-, m-, and o-isomers.

The ratio of the solvent to the reactants is in the range of 5:1 to 15:1 volume/weight (v/w). The preferred ratio is 10:1.

The acid catalyst is used to drive the reaction in one step and the type generally employed is a Bronsted acid. Examples of acid catalysts that can be employed include p-toluenesulfonic acid and its hydrates, methanesulfonic acid and sulfuric acid. The preferred is p-toluenesulfonic acid monohydrate.

The ratio of the catalyst to the reactant, 2-aminobenzonitrile, is in the range of 1.02 to 1.6 mole/mole. The preferred ratio is 1.02.

The synthesis of the invention is generally carried out at a temperature of about 110° C. to about 180° C. The preferred temperature range for carrying out the synthesis is about 130° C. to about 150° C., especially about 145° C.

The reaction generally takes about 10 to 15 hours to complete. However, the preferred reaction time is 11 to 12 hours.

The invention is described in greater detail in the following example in which all parts, proportions, ratios and percentages are by weight unless otherwise indicated.

EXAMPLE 1

Synthesis of 9-Amino-1,2,3,4-tetrahydroacridine

To a 200 ml, 3-neck round-bottom flask equipped with an overhead stirrer, Dean-Stark trap and thermometer was charged 6.67 g of 2-aminobenzonitrile, 66.7 ml of xylenes and 0.213 g of p-toluenesulfonic acid monohydrate. The stirred solution was heated to reflux. At reflux, a solution of 8.78 ml of cyclohexanone in 8.8 ml of xylenes was added dropwise over 40 minutes with simultaneous removal of water by azeotropic distillation. The mixture was refluxed for another 10 hours, then cooled slightly, and another 10.71 g of p-toluenesulfonic acid monohydrate was added and the mixture refluxed for another 5 hours. After cooling to room temperature, the crude product was isolated by filtration and drying under vacuum to yield 20.4 g of a solid. 19 g of this material was partitioned between 95 ml of dichloromethane and 38 ml of 5% aq sodium hydroxide. The basic aqueous phase was extracted with another 47.5 ml of dichloromethane and the combined organic phase was washed with 75 ml of water. The solution was stirred with 0.56 g of activated charcoal and 11 g of potassium carbonate, filtered through Celite, rinsed with dichloromethane and the filtrate was concentrated on a rotary evaporator to yield 9.7 g (93.4% overall yield) of the desired product, 9-amino-1,2,3,4-tetrahydroacridine, as a solid, which is >99% pure by GC analysis.

EXAMPLE 2

Conversion of Tacrine Free Base to Tacrine Hydrochloride

Tacrine (free base, 10 g) in 6N hydrochloric acid (50 ml) is stirred and heated until all of the solid dissolves. The hot solution is decanted to a clean flask and acetonitrile (50 ml) is added. The HCl salt of tacrine precipitates upon cooling and this solid is isolated at 0° C. and dried under vacuum to give a 90% recovery of a solid.

The tacrine HCl salt (7 g) is recrystallized from 3:1 (vol/vol) acetonitrile/water (42 ml). After the solid has precipitated, more acetonitrile (28 ml) is added to make the slurry more stirrable. The solid is isolated at 0° C. and dried under vacuum to give a 90% recovery of a solid (>99.9% pure by HPLC analysis).

We claim:

1. A method of preparing 9-amino-1,2,3,4-tetrahydroacridine which comprises reacting 2-aminobenzonitrile and cyclohexanone in the presence of an acid catalyst selected from p-toluenesulfonic acid monohydrate, methanesulfonic acid or sulfuric acid in a suitable solvent.

2. The method of claim 1 wherein the solvent is selected from xylenes, toluene, aromatic ethers such as anisole and dimethoxybenzene and halogenated aromatics such as chlorobenzene and dichlorobenzene.

3. The method of claim 2 wherein the solvent is xylenes.

4. The method of claim 1 wherein the acid catalyst is p-toluenesulfonic acid monohydrate and the solvent is xylenes.

5. The method of claim 1 wherein the free base product is converted to the hydrochloride salt by reacting the free base with hydrochloric acid.

* * * * *